United States Patent [19]

Exner et al.

[11] Patent Number: 4,814,322
[45] Date of Patent: Mar. 21, 1989

[54] SCENTS, AND SCENT COMPOSITIONS CONTAINING THEM

[75] Inventors: Fritz Exner, Holzminden; Detlef Hagena, Hoexter; Rudolf Hopp; Jürgen Nienhaus, both of Holzminden; Wilhelm Göttsch, Bevern, all of Fed. Rep. of Germany

[73] Assignee: Haarmann & Reimer GmbH, Holzminden, Fed. Rep. of Germany

[21] Appl. No.: 172,733

[22] Filed: Mar. 23, 1988

[30] Foreign Application Priority Data

Apr. 9, 1987 [DE] Fed. Rep. of Germany ....... 3712075

[51] Int. Cl.⁴ ............................................... A61K 7/46
[52] U.S. Cl. ...................................... 512/25; 568/673; 568/672
[58] Field of Search ............... 568/673, 672, 852, 857; 512/25

[56] References Cited

U.S. PATENT DOCUMENTS 3,754,936  8/1973  Epstein ................................. 568/672
4,533,761  8/1985  Peterson ............................... 568/673

FOREIGN PATENT DOCUMENTS 2407898  9/1974  Fed. Rep. of Germany ...... 568/673

OTHER PUBLICATIONS

Bloodworth et al., J. Chem. Soc., Perkin Trans 1, 1981 (12) pp. 3265–3271 (1981).

Primary Examiner—James H. Reamer
Attorney, Agent, or Firm—Sprung Horn Kramer & Woods

[57] ABSTRACT

The invention relates to 1,2-dialkoxyalkenes of the formula

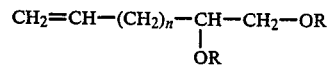

in which
  R denotes an alkyl group having 1 to 3 carbon atoms, and
  n denotes an integer from 2 to 8 and to the use of 1,2-dialkoxyalkanes and -alkenes of the formula

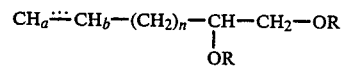

in which
  R denotes an alkyl group having 1 to 3 carbon atoms,
  n denotes an integer from 2 to 8, and

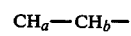

denotes the $CH_3-CH_2-$ or $CH_2=CH-$ group, as scents.

4 Claims, No Drawings

SCENTS, AND SCENT COMPOSITIONS CONTAINING THEM

The invention relates to new scents, and to scent compositions which contain these new scents.

It has been found that compounds of the general formula $$CH_a\text{---}CH_b\text{---}(CH_2)_n\text{---}\underset{\underset{OR}{|}}{CH}\text{---}CH_2\text{---}OR \qquad (I)$$

in which

R denotes an alkyl group having 1 to 3 carbon atoms,
n denotes a number from 2 to 8, and $$CH_a\text{---}CH_b\text{---}$$

denotes the $CH_3\text{---}CH_2$ or $CH_2\text{=}CH\text{---}$ group,
are valuable scents and are suitable for the production of scent compositions.

The invention therefore relates to the use of these 1,2-dialkoxyalkanes and -alkenes of the formula I as scents, and to scent compositions containing these compounds.

Some of the 1,2-dialkoxyalkanes of the formula I are described as intermediates in chemical reactions (see J. Chem. Soc., Perkin Trans. I 1981, 3265; J. Chem. Soc., Perkin Trans. I 1974, 1936; Tetrahedron Lett. 1970, 5275; Tetrahedron Lett. 1983, 4347). Nothing was hitherto known on the sensory properties of these alkanes, for example their scent properties.

The 1,2-dialkoxyalkenes of the formula I are new compounds. The invention therefore also relates to the compounds of the formula I in which $$CH_a\text{---}CH_b$$

represents the $CH_2\text{=}CH$ group. Of these new compounds, 1,2-dimethoxyoct-7-ene is distinguished by particularly valuable scent properties.

The scents of the formula I according to the invention can be prepared from the corresponding diols with the aid of known etherification processes (see for example, Houben-Weyl, Methoden der organischen Chemie [Methods of Organic Chemistry], Oxygen Compounds I, part 3, pages 24 ff, in particular pages 33 to 36). It has proven particularly advantageous to convert the diol into the sodium alcoholate using sodium hydride in a solvent such as toluene or xylene, sodium hydride being employed in an amount from 2 to 2.5 moles, preferably 2.2 moles, per mole of diol. After completion of hydrogen evolution, the alkylation is then carried out using the appropriate dialkyl sulphate at temperatures between 80° and 150° C., preferably between 110° and 130° C. The dialkyl sulphate is employed in an amount from 2 to 2.5 moles, perferably 2.2 moles, per mole of diol.

The fragrance of some of the scents according to the invention can be represented by the following fragrance descriptions:

1,2-dimethoxyhexane;
mushroomy, green, chemical
1,2-dimethoxyoctane:
green, waxy, reminscent of lilac, rose, mignonette and leaf green
1,2-diethoxyoctane:
fatty, green, olibanum, rancid
1,2-dimethoxyoct-7-ene:
green-herbaceous, broom, galbanum, vegetable
1,2-dimethoxydecane:
fatty, aldehydic
1,2-dimethoxydodecane:
orange, fatty, farnesol The scents according to the invention can be combined with other scents which are known per se, as described, for example, in Arctander, Perfume and Flavor Chemicals, Montclair, N.J. (U.S.A.) 1969, and ethereal oils, as described, for example, in Arctander, Perfume and Flavor Materials of natural Origin, Elisabeth, N.J. (U.S.A.) 1960, to give scent compositions having highly expressive notes. They are particularly suitable for increasing the naturalness of the fragrance of synthetic flower oils, such as lilac, hyacinth, jasmine etc. and for increasing the natural green fragrance in herbaceous and spicy-fruity fragrance complexes. Dosage in the scent compositions is 0.5 to 20%, preferably 1 to 10% by weight based on the total weight of the scent compositions.

Though some of the 1,3-dioxolanes disclosed as scents by DE-OS (German Published Specification) No. 3,004,661 have similar scent properties, they have the disadvantage that they are only stable in a basic medium and can therefor not be used in such important areas of application as acidic household cleansers, dishwashing agents, dishwasher detergents, wave sets, hair conditioners, hair shampoos, bleaching and tan creams and antiperspirants. The scent compositions produced using the compounds according to the invention are highly suitable for perfuming finished products in the cosmetics, fine perfumery, aerosol, cleansers and, in particular, the chemical-industrial sector, for example for detergents, hair-care agents, bubble baths, bath salt, dish-washing agents, dishwasher detergents, shampoos, fabric softeners, washing powders, soaps, antiperspirants, powders, creams, pre-shave lotions, aftershave lotions, air fresheners, WC cleansers, air freshener sprays, antiperspirant sprays, deodorant sprays, body sprays, insecticide sprays and sum screens.

The scent compositions and the perfumed products are produced in a conventional fashion, for example by mixing the components.

EXAMPLE 1

198 g (6.6 mol) of sodium hydride (80% strength) and 500 g of toluene are introduced into a flask, and the mixture is heated to the reflux temperature. 432 g (3 mol) of 7-octene-1,2-diol, dissolved in 1,500 g of toluene, are then added over 3 hours, and the mixture is stirred at the reflux temperature until hydrogen evolution is complete. 830 g (6.6 mol) of dimethyl sulphate are added over 4 hours, and the mixture is stirred for a further 2 hours. After addition of 50 ml of methanol, 1,500 g of water are added in order to dissolve the precipitate. The phases are separated and the organic phase is distilled. 420 g of 1,2-dimethoxyoct-7-ene having a boiling point of 80° C./10 mbar, corresponding to a yield of 81% of theory) are obtained.

The following were prepared analogously:

| | | |
|---|---|---|
| 1,2-dimethoxyhexane: | 82% yield, b.p.: | 75° C./30 mbar |

| -continued | | |
|---|---|---|
| 1,2-dimethoxyoctane: | 80% yield, b.p.: | 80° C./10 mbar |
| 1,2-diethoxyoctane: | 80% yield, b.p.: | 96° C./10 mbar |
| 1,2-dimethoxydecane: | 84% yield, b.p.: | 90° C./2 mbar |
| 1,2-dimethoxydodecane: | 80% yield, b.p.: | 95° C./1 mbar |

EXAMPLE 2

A perfume oil having a lilac note is produced by mixing the following components:

| Alpha-terpineol | 30.0 |
|---|---|
| Hydroxycitronellal | 20.0 |
| Phenylethyl alcohol | 15.0 |
| Heliotropin | 10.0 |
| Cinnamyl alcohol | 3.0 |
| Anisaldehyde | 2.0 |
| Linalool | 9.0 |
| Phenylacetaldehyde, 50% strength in phenylethyl alcohol | 1.0 |
| 1,2-dimethoxyoctane | 1.0 |
| Dipropylene glycol | 9.0 |
| | 100.0 parts by weight |

EXAMPLE 3

A perfume oil having an orange note is produced by mixing the following components:

| Citral | 4.0 |
|---|---|
| Decylaldehyde | 6.0 |
| Dodecylaldehyde | 0.5 |
| Myristaldehyde, 50% strength in diethyl phthalate | 0.5 |
| Octylaldehyde | 0.2 |
| Undecylaldehyde | 1.0 |
| Heptanal, 10% strength in diethyl phthalate | 0.5 |
| Hexanal, 10% strength in diethyl phthalate | 0.5 |
| Linalool | 5.0 |
| Citronellal | 0.4 |
| Ginger grass oil | 0.2 |
| Nonanal | 0.2 |
| Nonanol | 1.0 |
| Trimethylundecylenealdehyde | 1.0 |
| Orange oil, (Brasilian) | 50.0 |
| Alpha-terpineol | 2.0 |
| Myrcene | 0.5 |
| Carvone | 1.0 |
| Nerol | 1.0 |
| Neryl acetate | 1.0 |
| 1,2-dimethoxyoctane | 10.0 |
| Dipropylene glycol | 13.5 |
| | 100.0 parts by weight |

What is claimed is:

1. A scented composition comprising as one component 0.5 to 20% by weight based on the total weight of the scented composition at least one 1,2-dialkoxyalkane or -alkene of the formula

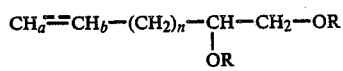

in which
R is an alkyl group having 1 to 3 carbon atoms,
n is an integer from 2 to 8, and

denotes the $CH_3$—$CH_2$— or $CH_2$=$CH$— group.

2. A method of altering the scent of a scent composition or of a perfumed product which comprises incorporating into this scent composition or perfumed product at least one 1,2-dialkoxyalkane or -alkene of the formula

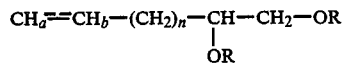

in which
R is an alkyl group having 1 to 3 carbon atoms,
n is an integer from 2 to 8, and

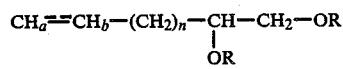

denotes the $CH_3$—$CH_2$— or $CH_2$=$CH$— group, said dialkoxyalkane or -alkene being present in an amount of 0.5 to 20% by weight based on the total weight of the scent composition or perfumed product.

3. A 1,2-dialkoxyalkene of the formula

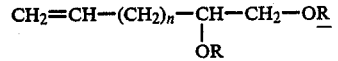

in which
R is an alkyl group having 1 to 3 carbon atoms, and
n is an integer from 2 to 8.

4. 1,2-dimethoxyoct-7-ene.

* * * * *

UNITED STATES PATENT AND TRADEMARK OFFICE
CERTIFICATE OF CORRECTION

PATENT NO. : 4,814,322
DATED : March 21, 1989
INVENTOR(S) : Fritz Exner, et al

It is certified that error appears in the above-identified patent and that said Letters Patent is hereby corrected as shown below:

| | |
|---|---|
| Title Page, Abstract, 4th line from bottom | Delete "$CH_a\text{---}CH_b$" and substitute --$CH_a$=$CH_b$-- |
| Title Page, Abstract third line from bottom | Delete "$CH_2$50 CH-" and substitute --$CH_2$=CH- -- |
| Col. 1, lines 11, 19 and 40 | Delete "$CH_a$---" and substitute --$CH_a$= -- |
| Col. 2, line 46 | Delete "sum" and substitute --sun-- |
| Col. 4, line 37 | Delete "$CH_a$=$CH_b\text{-}(CH_2)_n\text{-}\underset{\underset{OR}{|}}{CH}\text{-}CH_2\text{-}OR$" and substitute --$CH_a$=$CH_b$- -- |
| Col. 4, line 48 | Delete "-OR" and substitute -- -OR -- |

Signed and Sealed this

Twelfth Day of December, 1989

*Attest:*

JEFFREY M. SAMUELS

*Attesting Officer*     *Acting Commissioner of Patents and Trademarks*